Figure 1:
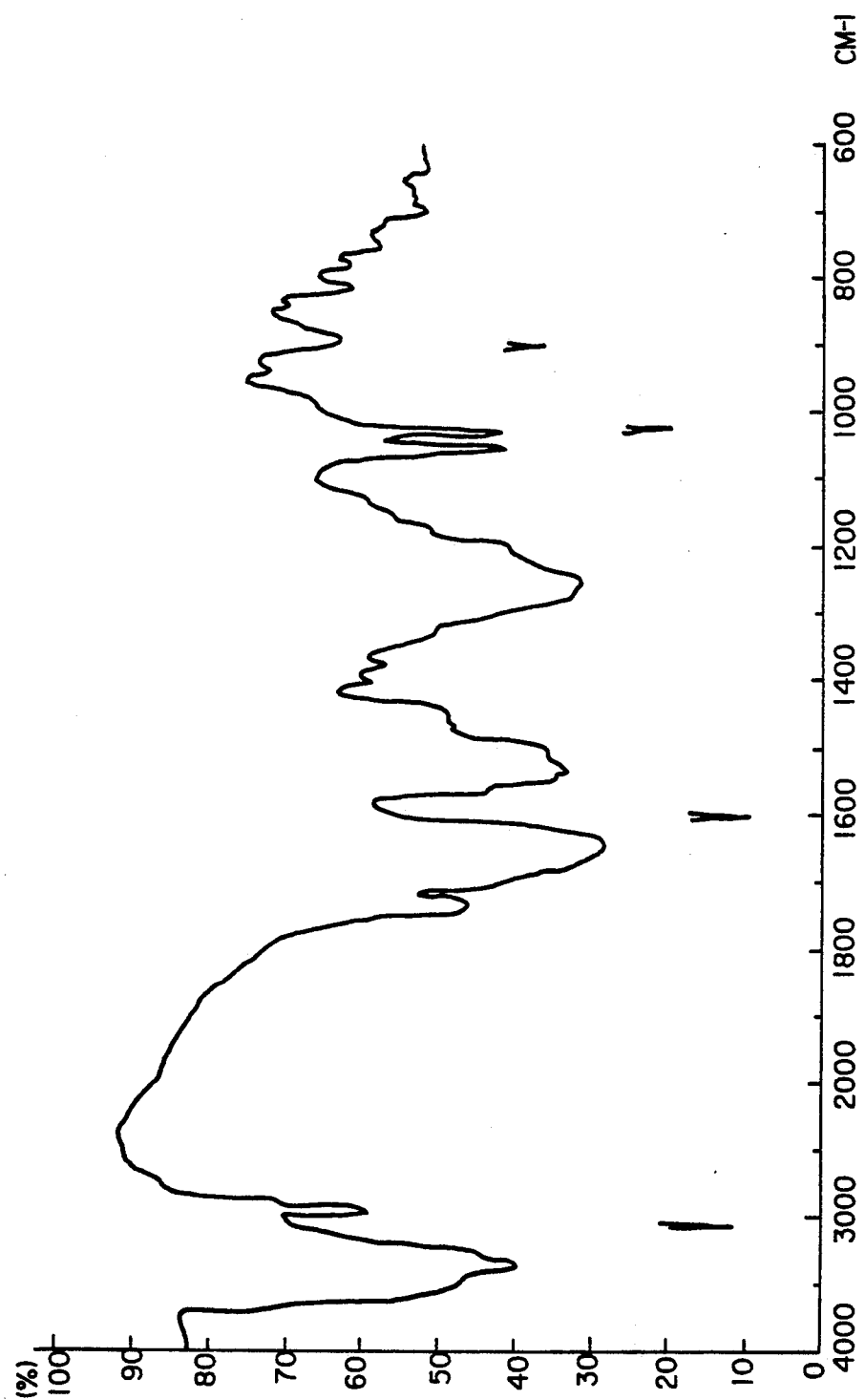

United States Patent [19]

Inamura et al.

[11] Patent Number: 5,279,826
[45] Date of Patent: Jan. 18, 1994

[54] PROPHYLACTIC/THERAPEUTIC COMPOSITION FOR DISSEMINATED INTRAVASCULAR COAGULATION, CHRONIC RESPIRATORY TRACT INFECTIOUS DISEASE OR CHRONIC BRONCHITIS

[75] Inventors: Noriaki Inamura, Moriya; Yasuhiko Shinguh; Kunio Nakahara, both of Tsukuba; Yoshitada Notsu, Tsuchiura; Masanori Okamoto, Tsukuba; Shigehiro Takase, Ishioka; Hiroshi Hatanaka, Moriya; Masami Ezaki, Tsukuba; Eisaku Tsujii, Tsukuba; Nobuharu Shigematsu, Tsukuba; Masakuni Okuhara, Tsukuba, all of Japan

[73] Assignee: Fujisawa Pharmaceutical Co., Ltd., Osaka, Japan

[21] Appl. No.: 899,915

[22] Filed: Jun. 17, 1992

[30] Foreign Application Priority Data

Jun. 18, 1991 [JP] Japan ................................ 3-245283

Dec. 19, 1991 [JP] Japan ................................ 3-361135

[51] Int. Cl.$^5$ ............................................ H61K 35/74
[52] U.S. Cl. ...................................................... 424/117
[58] Field of Search ........................................ 424/117

[56] References Cited

U.S. PATENT DOCUMENTS 5,021,240 6/1991 Hatanaka et al. .

FOREIGN PATENT DOCUMENTS 0465895 1/1992 European Pat. Off. .

*Primary Examiner*—Jerome D. Goldberg
*Attorney, Agent, or Firm*—Oblon, Spivak, McClelland, Maier & Neustadt

[57] ABSTRACT

A method for therapy of disseminated intravascular coagulation, or chronic respiratory tract infectious disease characterized by administering to a patient in need thereof an effective dose suitable for therapeutic treatment of said condition of WS7622A mono- or di-sulfate ester or their pharmaceutically acceptable salt.

3 Claims, 5 Drawing Sheets

1H NUCLEAR MAGNETIC RESONANCE SPECTRUM OF WS7622A DISULFATE ESTER DISODIUM SALT

INFRARED ABSORPTION SPECTRUM OF
WS7622A DISULFATE ESTER DIPOTASIUM SALT

1H NUCLEAR MAGNETIC RESONANCE SPECTRUM OF WS7622A DISULFATE ESTER DIPOTASIUM SALT

PROPHYLACTIC/THERAPEUTIC COMPOSITION FOR DISSEMINATED INTRAVASCULAR COAGULATION, CHRONIC RESPIRATORY TRACT INFECTIOUS DISEASE OR CHRONIC BRONCHITIS

This invention relates to a prophylactic/therapeutic composition for disseminated intravascular coagulation, chronic respiratory tract infectious disease or chronic bronchitis comprising WS7622A mono- or disulfate ester or a pharmaceutically acceptable salt thereof as an active ingredient.

The same inventors of this invention previously invented a pharmaceutical composition comprising WS7622A mono- or disulfate ester having human leukocyte elastase inhibitory activity (European Patent Application No. 91110243.2). Now, the inventors of this invention have completed an invention directed to new medicinal uses for WS7622A mono- or disulfate ester or a pharmaceutically acceptable salt thereof which were not disclosed in the specification of the above application.

This invention relates to a prophylactic and therapeutic composition for disseminated intravascular coagulation (DIC), chronic respiratory tract infectious disease, or chronic bronchitis, which comprises WS7622A mono- or disulfate ester or a pharmaceutically acceptable salt thereof as an active ingredient.

WS7622A mono- and disulfate esters and pharmaceutically acceptable salts thereof, which are employed in this invention, are known compounds European Publication No. 0465895 A1 which corresponds to U.S. application Ser. No. 07/713,295 and can be produced by converting WS7622A or a salt thereof (European publication No. 0387712 A1 U.S. application No. 07/645,820), to the corresponding sulfuric acid esters. Of these compounds, WS7622A disulfate ester disodium salt and WS7622A disulfate ester dipotassium salt have the following physicochemical properties.

WS7622A disulfate ester disodium salt (disodium salt of WS7622A disulfate) :

Appearance : Colorless crystals

Solubility : Soluble; water, methanol. Insoluble; chloroform, n-hexane.

Melting point: 257°–263° C. (decompn.)

Specific rotation : $[\alpha]^{23}_D + 37.5°$ (C=1.0, methanol)

Molecular formula : $C_{47}H_{61}N_9O_{19}S_2Na_2$

Elemental analysis : Calcd.: (for $C_{47}H_{61}N_9O_{19}S_2Na_2 \cdot 6H_2O$) C 44.30, H 5.77, N 9.89, S 5.03, Na 3.61%; Found : C 44.98, H 5.90, N 10.06, S 5.00, Na 3.98%.

Molecular weight : FAB-MS m/z 1188 (M+Na)+

Thin-layer chromatography :

| Stationary phase | Developing solvent | Rf value |
|---|---|---|
| Silica gel (Merck Art 5715) | $CHCl_3$—$CH_3OH$—$H_2O$ (65:25:4) | 0.11 |
| | n-Butanol-acetic acid-water (4:2:1) | 0.29 |

Figure 2:
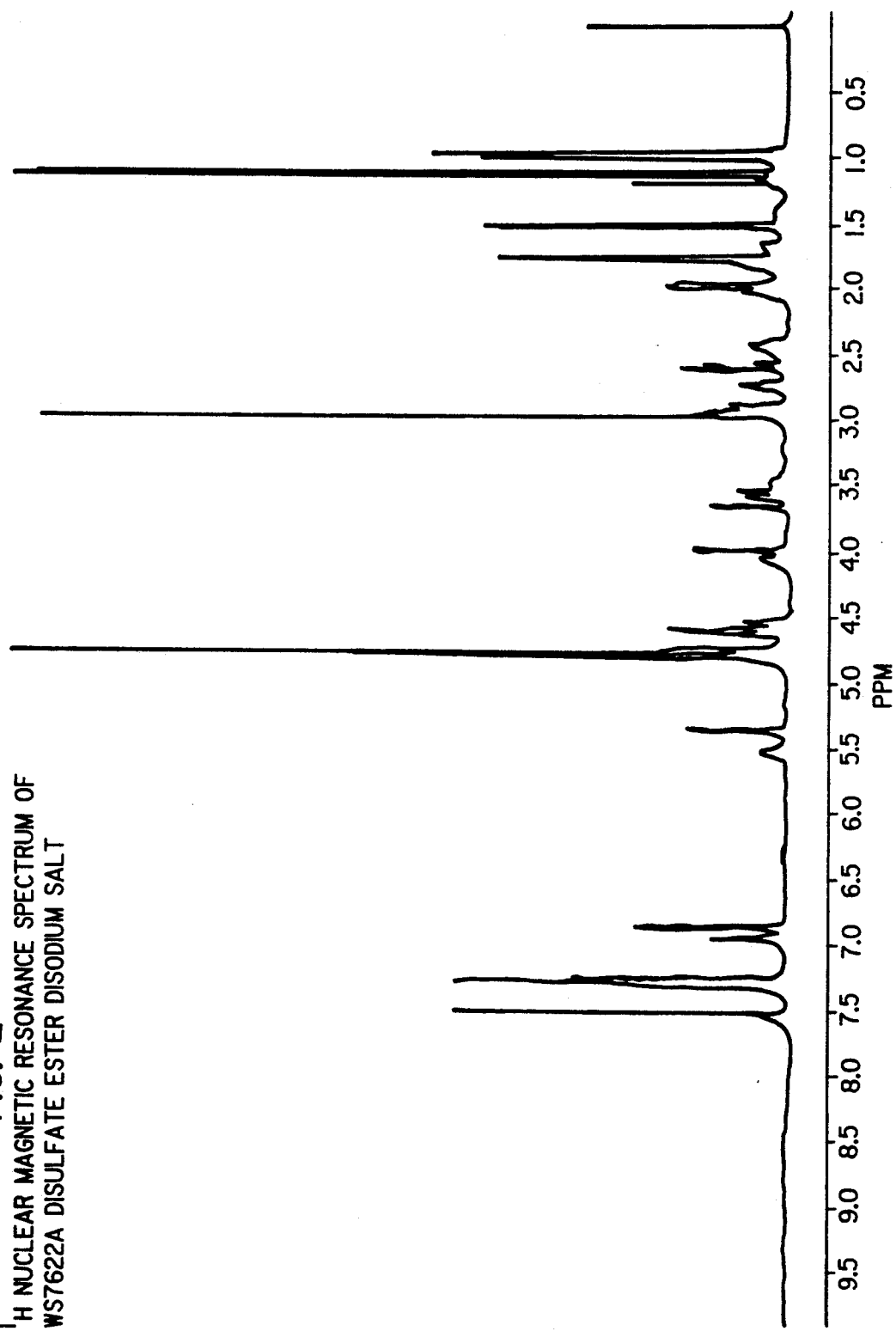

Infrared absorption spectrum (attached FIG. 1) : $\nu_{max}^{KBr}$ 3360, 2960, 1735, 1660, 1640, 1530, 1500, 1380, 1250, 1200, 1060, 1030, 940, 890 cm$^{-1}$ $^1$H Nuclear magnetic resonance spectrum (attached FIG. 2) :

| (400 MHz, $D_2O$)δ | |
|---|---|
| 7.50 | (1H, s) |
| 7.27 | (1H, s) |
| 7.33–7.24 | (3H, m) |
| 6.94 | (1H, q, J=7Hz) |
| 6.85 | (2H, br d, J=8Hz) |
| 5.53 | (1H, m) |
| 5.37 | (1H, m) |
| 4.80 | (1H, br s) |
| 4.63–4.57 | (2H, m) |
| 4.53 | (1H, m) |
| 4.06 | (1H, m) |
| 3.99 | (1H, d, J=10Hz) |
| 3.56 | (1H, br d, J=14Hz) |
| 3.46 | (1H, m) |
| 2.97 | (3H, s) |
| 2.97–2.88 | (2H, m) |
| 2.72 | (1H, m) |
| 2.59 | (1H, m) |
| 2.51–2.38 | (2H, m) |
| 2.09–1.91 | (4H, m) |
| 1.82–1.60 | (3H, m) |
| 1.77 | (3H, d, J=7Hz) |
| 1.50 | (3H, d, J=6.5Hz) |
| 1.40 | (1H, m) |
| 1.11 | (6H, d, J=7Hz) |
| 0.99 | (3H, d, J=6.5Hz) |
| 0.97 | (3H, d, J=6.5Hz) |

Figure 3:
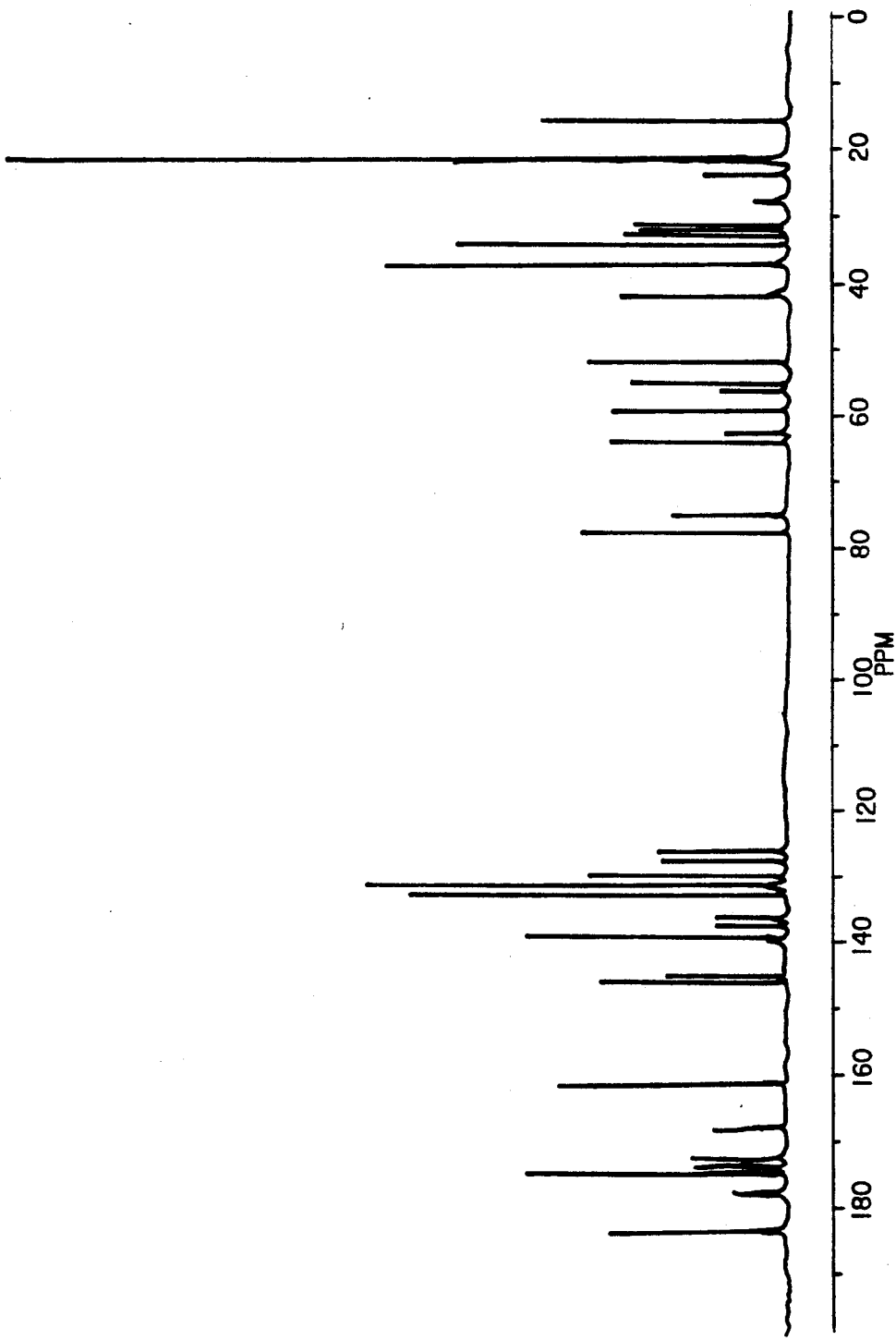

$^{13}$C Nuclear magnetic resonance spectrum (attached FIG. 3) :

| (100 MHz, $D_2O$)δ | |
|---|---|
| 183.6 | (s) |
| 177.9 | (s) |
| 177.7 | (s) |
| 174.8 | (s) |
| 173.8 | (s) |
| 173.3 | (s) |
| 172.4 | (s) |
| 167.8 | (s) |
| 161.5 | (s) |
| 145.5 | (s) |
| 144.9 | (s) |
| 139.6 | (d) |
| 139.0 | (s) |
| 137.0 | (s) |
| 136.0 | (s) |
| 132.3 | (d) × 2 |
| 131.0 | (d) × 2 |
| 129.6 | (d) |
| 127.4 | (d) |
| 125.9 | (d) |
| 77.4 | (d) |
| 75.1 | (d) |
| 63.8 | (d) |
| 62.7 | (d) |
| 59.1 | (d) |
| 55.9 | (d) |
| 54.9 | (d) |
| 51.9 | (d) |
| 41.9 | (t) |
| 37.2 | (d) |
| 36.9 | (t) |
| 34.1 | (q) |
| 32.3 | (d) |
| 31.9 | (t) |
| 31.8 | (t) |
| 31.2 | (t) |
| 27.5 | (t) |
| 23.7 | (t) |
| 21.7 | (q) |
| 21.4 | (q) × 2 |
| 21.3 | (q) |
| 21.1 | (q) |
| 15.5 | (q) |

Amino Acid Analysis

WS7622A disulfate ester disodium salt (1 mg) was hydrolyzed with 6 N-hydrochloric acid (1 ml) at 110° C. for 20 hours and the hydrolyzate was concentrated to dryness and analyzed with a Hitachi 835 automatic amino acid analyzer. As the amino acid reference standards, Wako Pure Chemical's Type H (Wako Code 013-08391) and Type B (016-08641) were used.

As a result, threonine, valine, phenylalanine, ornithine, ammonia and several unknown ninhydrin-positive substances were detected.

The following partial structural formula is proposed for WS7622A disulfate ester disodium salt.

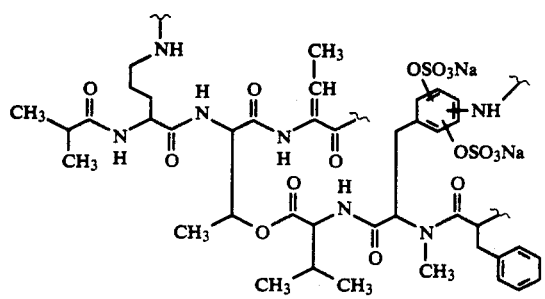

WS7622A disulfate ester dipotassium salt (dipotassium salt of WS7622A disulfate):
  Appearance: Colorless amorphous powder
  Solubility: Soluble; water, methanol. Insoluble; chloroform, n-hexane.
  Melting point: 230°-237° C. (decompn.)
  Specific rotation: $[\alpha]^{23}_D + 34°$ (C=1.0, methanol)
  Molecular formula: $C_{47}H_{61}N_9O_{19}S_2K_2$
  Elemental analysis: Calcd.: (for $C_{47}H_{61}N_9O_{19}S_2K_2 \cdot 6H_2O$) C 43.21, H 5.63, N 9.65, S 4.91, K 5.99%; Found: C 43.96, H 5.44, N 9.97, S 5.09, K 4.49%.
  Molecular weight: FAB-MS m/z 1236 (M+K)+
  Thin-layer chromatography:

| Stationary phase | Developing solvent | Rf value |
|---|---|---|
| Silica gel (Merck Art 5715) | $CHCl_3$—$CH_3OH$—$H_2O$ (65:25:4) | 0.13 |

Figure 4:
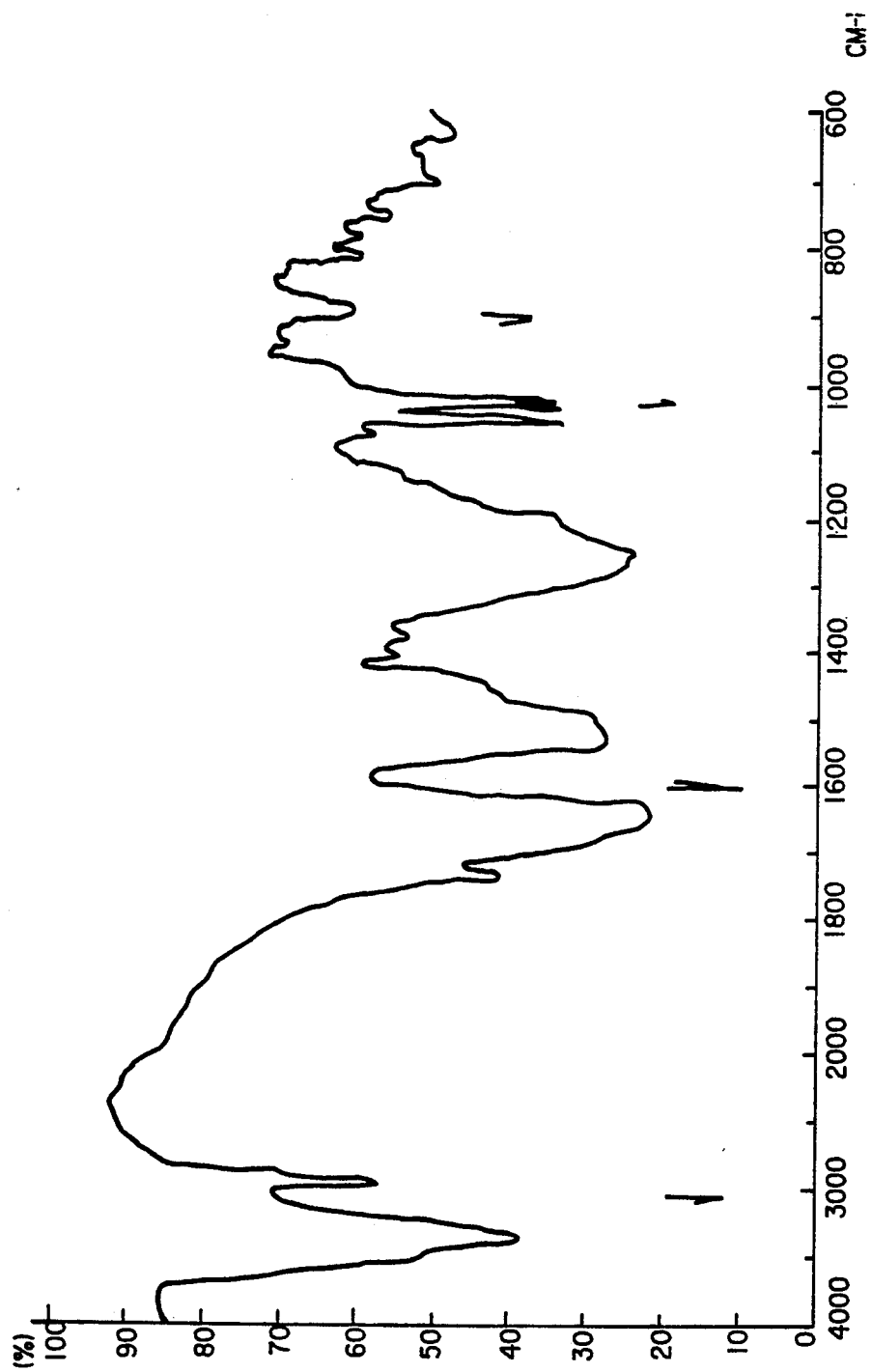
Figure 5:
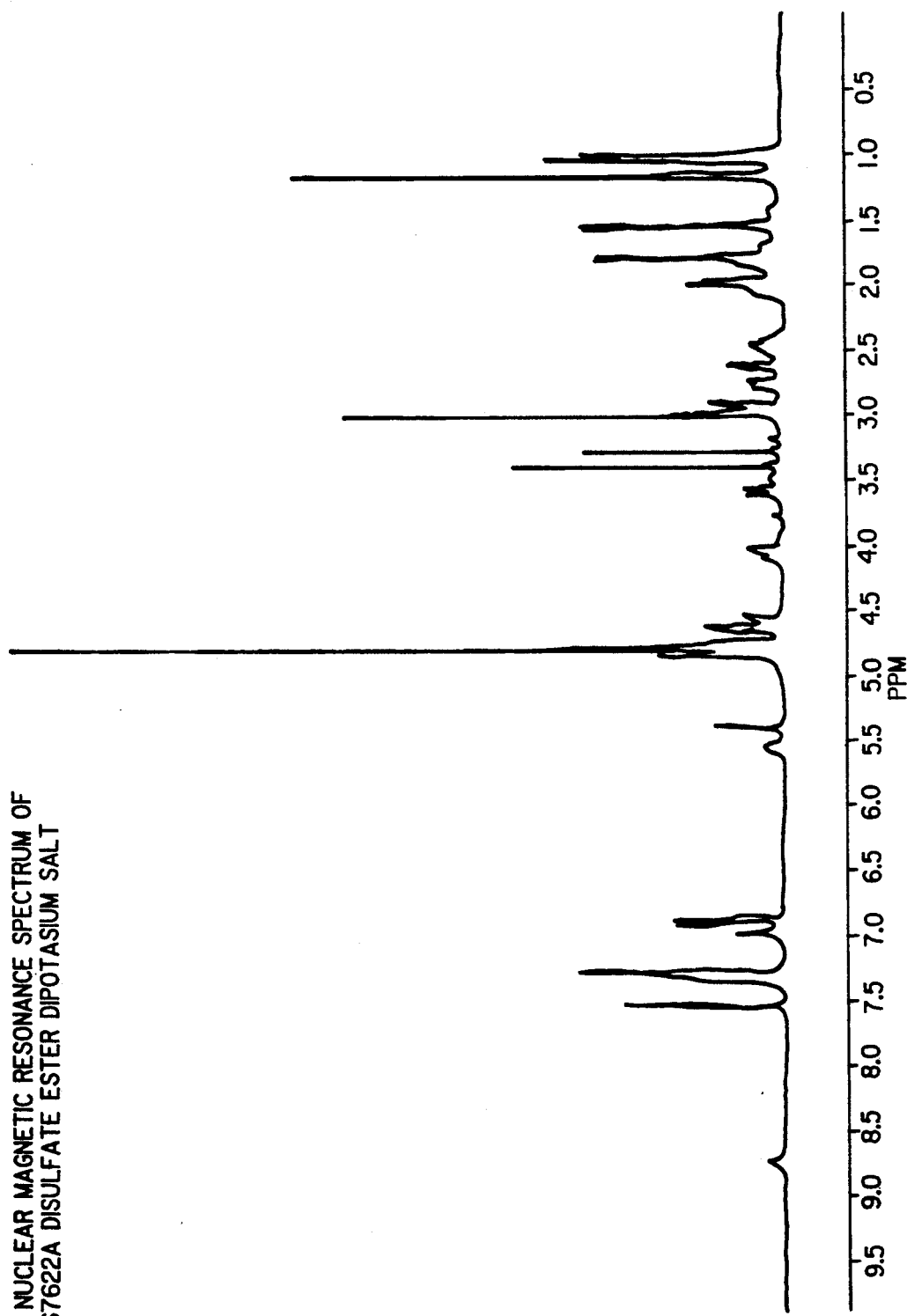

Infrared absorption spectrum (attached FIG. 4):
$\nu_{max}^{KBr}$ 3360, 2960, 1735, 1660, 1640, 1530, 1500, 1405, 1380, 1250, 1200, 1050, 1030, 940, 890 cm$^{-1}$ $^1$H Nuclear magnetic resonance spectrum (attached FIG. 5):

| (400 MHz, $D_2O$)δ | |
|---|---|
| 7.52 | (1H, s) |
| 7.28 | (1H, s) |
| 7.34–7.25 | (3H, m) |
| 6.96 | (1H, q, J=7Hz) |
| 6.87 | (2H, br d, J=8Hz) |
| 5.56 | (1H, m) |
| 5.40 | (1H, m) |
| 4.84 | (1H, br s) |
| 4.70–4.55 | (3H, m) |
| 4.10 | (1H, m) |
| 4.03 | (1H, m) |
| 3.60 | (1H, br d, J=14Hz) |
| 3.50 | (1H, m) |
| 3.00 | (3H, s) |
| 3.00–2.85 | (2H, m) |
| 2.76 | (1H, m) |
| 2.62 | (1H, m) |
| 2.55–2.40 | (2H, m) |
| 2.12–1.95 | (4H, m) |
| 1.90–1.65 | (3H, m) |
| 1.79 | (3H, d, J=7Hz) |
| 1.53 | (3H, d, J=6.5Hz) |
| 1.45 | (1H, m) |
| 1.14 | (6H, d J=7Hz) |
| 1.02 | (3H, d J=6.5Hz) |
| 1.00 | (3H, d J=6.5Hz) |

Amino Acid Analysis

WS7622A disulfate ester dipotassium salt (1 mg) was hydrolyzed with 6 N-hydrochloric acid (1 ml) at 110° C. for 20 hours and the hydrolyzate was concentrated to dryness and analyzed with a Hitachi 835 automatic amino acid analyzer. As the amino acid reference standards, Wako Pure Chemical's Type H (Wako Code 013-08391) and Type B (016-08641) were used.

As a result, threonine, valine, phenylalanine, ornithine, ammonia and several unknown ninhydrin-positive substances were detected.

The following partial structural formula is proposed for WS7622A disulfate ester dipotassium salt.

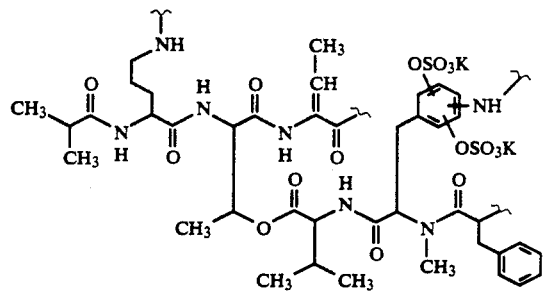

The pharmaceutically acceptable salt of WS7622A mono- or disulfate ester includes mono- or disalts with inorganic or organic bases such as alkali metal salts (e.g. sodium salt, potassium salt, etc.), alkaline earth metal salts (e.g. calcium salt etc.), ammonium salt, ethanolamine salt, triethylamine salt, dicyclohexylamine salt, pyridine salt and so on.

WS7622A mono- and disulfate esters and pharmaceutically acceptable salts thereof are of use as prophylactic-therapeutic agents for disseminated intravascular coagulation (DIC), chronic respiratory tract infectious disease and chronic bronchitis, and further are expected to be of use as prophylactic/therapeutic agents for arthrosclerosis, periodontitis, pulmonary fibrosis, chronic obstructive pulmonary disease, diffuse panbronchiolitis, hydroa, shock, systemic lupus erythematosus (SLE), Crohn's disease, amniorrhexis (premature labor), ischemic reperfusion disorder, systic fibrosis, bronchiectasia, and/or corneal cicatrization or fibroblast growth [ocular coagulation (burn, mechanical and chemical damages, keratoconjunctivitis) etc.].

As evidence of the usefulness of WS7622A mono- or disulfate ester or a pharmaceutically acceptable salt thereof, pharmacological test data on these compounds are presented below.

Test 1

Protease Inhibition Assay (1) Method

The buffer solution used throughout this assay was 0.5M NaCl-containing 0.1M HEPES [N-(2-hydroxyethyl)piperazine-N'-(2-ethanesulfonic acid)], pH 7.5. Using a 96-well microtiter plate, 25 μl of 2 mM methoxysuccinyl (Ala)$_2$-Pro-Val-p-nitroanilide (a 100 mM solution in dimethyl sulfoxide was diluted with the buffer solution) was mixed with 50 μl of the sample (10 μl of an organic solvent solution of the sample was diluted 5-fold with the buffer solution).

The absorbance of the mixture at a wavelength of 415 nm was measured with a microplate reader (Corona Electric, Ibaragi Prefecture). Then, 6 μg/ml of human sputum elastase (HSE) was added and the mixture was allowed to stand at room temperature for 30 minutes. The absorbance at 415 nm was then measured. The percent inhibition (%) by the drug was calculated from the formula: $100 \times (1 - r$ in the presence of an inhibitor/r in the absence of the inhibitor), wherein r represents the absorbance after 30 minutes' incubation *minus* the absorbance before addition of the enzyme.

The inhibitor activities against other proteases were assayed using N-succinyl-(Ala)$_3$-p-nitroanilide for swine pancreatic elastase (type IV, final concentration 5 μg/ml), N-alpha-benzoyl-Arg-p-nitroanilide for bovine pancreatic trypsin (type I, final conc. 16 μg/ml) and methoxysuccinyl-(Ala)$_2$-Pro-Met-p-nitroanilide for bovine pancreatic chymotrypsin (type II, final conc. 1.5 μg/ml). HSE was obtained from Elastin Products Co., Inc., Missouri, U.S.A. All other substrates and proteases were purchased from Sigma Chemicals Company.

Inhibitory activity of WS7622A disulfate ester disodium salt and WS7622A disulfate ester dipotassium salt against several kinds of serine proteases
(2) Results

| Substance (M) | Human sputum elastase | Swine pancreatic elastase | Trypsin (bovine) | Chymotrypsin (bovine) |
|---|---|---|---|---|
| | IC$_{50}$ (M) | | | |
| WS7622A disulfate ester disodium salt | $3.5 \times 10^{-8}$ | $4.9 \times 10^{-8}$ | $1.8 \times 10^{-4}$ | $2.0 \times 10^{-7}$ |
| WS7622A disulfate dipotassium salt | $5.9 \times 10^{-8}$ | $4.9 \times 10^{-8}$ | $2.0 \times 10^{-4}$ | $2.0 \times 10^{-7}$ |

Each inhibitory activity was expressed in 50% inhibitory concentration (IC$_{50}$).

Test 2

Effects on the endotoxin-induced disseminated intravascular coagulation (DIC) model (1) Method The rat model of DIC was constructed by the method of Nishikawa et al. (Life Science 39, 111, 1986). First, under pentobarbital anesthesia (50 mg/kg, i.p.), the right femoral vein of 7-week-old male Wistar rats was canulated with a PE-50 tube for infusion of endotoxin (LPS) and the drug. The normal group was infused with saline, while the control group was infused with 0.25 mg/kg/hr of endotoxin over a period of 4 hours. The drug treatment group was infused with a mixture of endotoxin and the drug, with the amount of the drug being set at 10 mg/kg/hr. All infusions were performed at the rate of 2.3 ml/hr.

(2) Results

| Treatment | n | PLT count ($\times 10^3$/mm$^3$) | PT (sec) | APTT (sec) | FIG (mg/dl) | FDP (μg/ml) |
|---|---|---|---|---|---|---|
| Normal group | 7 | 595 ± 9.3 | 13.4 ± 0.1 | 22.2 ± 0.2 | 215 ± 5.8 | 0.5 ± 0.0 |
| Control group | 10 | 273 ± 17.3 | 20.8 ± 1.6 | 66.0 ± 9.3 | 39 ± 4.9 | 6.0 ± 0.7 |
| WS7622A disulfate ester disodium salt | 7 | 318 ± 16.0 (14.1%) | 19.1 ± 1.0 (23.4%) | 52.8 ± 8.3 (30.0%) | 54 ± 8.7 (8.2%) | 5.0 ± 0.0 (18.2%) |

The figure in parentheses denotes % inhibition.
PLT : platelet
PT : prothrombin time
APTT: activated partial thromboplastin time
Fig : fibrinogen
FDP : fibrin and fibrinogen degradation products

Test 3

Determination of the Activity in Elastase-Induced Pulmonary Damage.

(1) Method

Hamsters under pentobarbital anesthesia were used. Saline or saline-containing human sputum elastase was instilled intratracheally via a small incision in the ventral neck region using 1 ml syringe with a 27-gauge needle. After 3 hours, animals were sacrificed by CO$_2$ asphyxiation, each animal's trachea was reexposed. The lungs were then laveged using a 2.5-ml aliquot of saline and then withdrawing the saline, yielding a final volume of approximately 1.5 ml bronchoalveolar lavage (BAC) fluid from each animal.

The cells of BAL fluid were collected by centrifugation and were then diluted with distilled water to disrupt, and the hemoglobin contents determined spectorphotometrically at 541 nm.

Test drugs were dissolved in salin and instilled intratracheally in the same manner as used to instill elastase, at 5 minutes before instillation of elastase.

(2) Results
Inhibitory effect on elastase-induced lung hemorrhage

| Test compound | 5 min predose (μg/site) | Hemorrhage (OD 541 nm) | % inhibition |
|---|---|---|---|
| Normal | — | 0.31 ± 0.12 | — |
| Control | — | 29.35 ± 2.9 | — |
| WS7622A disulfate ester disodium salt | 1 | 19.06 ± 1.40* | 35.4 |
| | 10 | 9.75 ± 4.82* | 67.5 |
| | 100 | 0.28 ± 0.05*** | 100.1 |
| WS7622A disulfate | 1 | 19.71 ± 1.20* | 33.2 |

-continued

(2) Results
Inhibitory effect on elastase-induced lung hemorrhage

| Test compound | 5 min predose (μg/site) | Hemorrhage (OD 541 nm) | % inhibition |
|---|---|---|---|
| ester dipotassium salt | 10 | 10.73 ± 1.20** | 64.1 |
|  | 100 | 0.35 ± 0.16*** | 99.9 |

*$p < 0.05$, $P < 0.01$, *$p < 0.001$ compared with control group (Student t test)

The pharmaceutical composition of this invention can be used in the conventional dosage forms such as powder, fine granule, granule, tablet, sugar-coated pill, microcapsule, capsule, suppository, solution, suspension, emulsion, syrup, injection, inhalant and so on. Where necessary, there may be incorporated in the composition a diluent or disintegrator (e.g. sucrose, lactose, starch, crystalline cellulose, low-substitution hydroxypropylcellulose, synthetic aluminum silicate, etc.), a binder (e.g. cellulose, methylcellulose, hydroxypropylcellulose, hydroxymethylpropylcellulose, polypropylpyrrolidone, polyvinylpyrrolidone, gelatin, gum arabic, polyethylene glycol, etc.), a colorant, a sweetener, a lubricant (e.g. magnesium stearate etc.) and so on.

Though dependent on the patient's age, body weight and clinical condition, among other factors, the pharmaceutical composition of this invention can be administered in a daily dose of 100 mg to 10 g and preferably 1 g to 5 g, as the claimed compound or pharmaceutically acceptable salt, which daily dose may be administered in 1–3 divided doses. Typical unit doses are 50 mg, 100 mg, 200 mg, 500 mg and 1 g.

We claim:

1. A method for therapy of disseminated intravascular coagulation, chronic respiratory tract infectious disease or chronic bronchitis characterized by administering to a patient in need thereof an effective does suitable for therapeutic treatment of said condition of WS7622A mono- or di-sulfate ester or their pharmaceutically acceptable salt.

2. The method of claim 1 wherein said di-sulfate ester is WS7622A disulfate ester disodium salt.

3. The method of claim 1 wherein said disulfate salt is WS7622A disulfate ester dipotassium salt.

* * * * *